United States Patent [19]

Lohse et al.

[11] 4,327,032
[45] Apr. 27, 1982

[54] ACICULAR ALUMINIUM SALTS OF CARBOXYLIC ACIDS AND PROCESSES FOR THEIR PREPARATION

[75] Inventors: Friedrich Lohse, Oberwil; Rolf Schmid, Gelterkinden; Willy Fatzer, Bottmingen all of Switzerland

[73] Assignee: Ciba-Geigy Corporation, Ardsley, N.Y.

[21] Appl. No.: 109,716

[22] Filed: Jan. 4, 1980

[30] Foreign Application Priority Data

Jan. 16, 1979 [CH] Switzerland ............................. 403/79
Jan. 16, 1979 [CH] Switzerland ............................. 404/79

[51] Int. Cl.$^3$ ................................................. C07F 5/06
[52] U.S. Cl. ..................................... 260/448 R; 524/399
[58] Field of Search ................................... 260/448 R

[56] References Cited

U.S. PATENT DOCUMENTS

| | | | |
|---|---|---|---|
| 801,158 | 10/1905 | Reiss | 260/448 R |
| 1,878,962 | 9/1932 | Meidert | 260/448 R |
| 2,011,292 | 8/1935 | Koch | 260/448 R |
| 2,086,499 | 7/1937 | Hennig | 260/448 R |
| 2,522,641 | 9/1950 | Schmerling | 260/448 R |
| 2,682,507 | 6/1954 | Agens | 260/448 R X |
| 2,965,662 | 12/1960 | Moser | 260/448 R |
| 2,992,262 | 7/1961 | Sears et al. | 260/448 R |

*Primary Examiner*—Helen M. S. Sneed
*Attorney, Agent, or Firm*—Harry Falber

[57] ABSTRACT

Aluminium monohydroxide salts of a carboxylic acid which are free from water of crystallization and have the formula

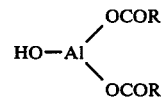

or contain the structural element of the formula

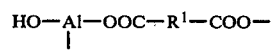

in which R is methyl, ethyl or phenyl or $R^1$ is the divalent group $-C_nH_{2n}-$, in which n is a number from 3 to 10, and which can also be in the form of a dimer, have an acicular to rod-shaped crystal form. They are suitable as fillers for polymers, especially as reinforcing fillers for elastomeric epoxide resins.

8 Claims, No Drawings

ACICULAR ALUMINIUM SALTS OF CARBOXYLIC ACIDS AND PROCESSES FOR THEIR PREPARATION

The invention relates to acicular and anhydrous aluminium monohydroxide salts of specific mono- or dicarboxylic acids and a process for their preparation.

Neutral and basic aluminium salts of carboxylic acids have already been known for a long time and have also been used industrially for a long time, for example as therapeutic agents or in dyeing. Inter alia, aluminium monohydroxide diacetate has also already been described, cf. Gmelins Handbuch der anorganischen Chemie (Gmelins Handbook of Inorganic Chemistry), 8th edition (No. 35), Part B (Aluminium), page 796. Depending on the process by which they are prepared, these diacetates have different contents of water of crystallisation.

The neutral and basic aluminium salts which are obtained from aluminium oxide or aluminium hydroxide and carboxylic acids, for example formic acid or acetic acid, or mixtures of acetic acid and tartaric acid, and are described in French Patent Specification No. 379,547 are also not free from water of crystallisation, since, with the indicated process of preparation, although it is stated that the reaction should be carried out with the exclusion of water, no precautionary measures are taken in order to remove the water of reaction. Investigations carried out by the applicant company have shown that the process of preparation carried out at room temperature cannot lead to anhydrous products.

Aluminium monohydroxide diacetate which contains water of crystallisation and is obtained from hydrated alumina and anhydrous acetic acid, and the use of this compound is dyeing and in medicine, are described in Austrian Patent Specification No. 61,179.

The products described in the prior art are amorphous or crystalline powders, and the crystallites do not possess a pronounced elongated form. However, acicular crystalline compounds are extremely desirable, especially as reinforcing fillers for plastics, and it is the object of the invention to provide acicular crystalline compounds of basic aluminium salts of carboxylic acids.

The invention relates to an acicular to rod-shaped aluminium monohydroxide salt of a carboxylic acid, which salt is free from water of crystallisation and has the formula I or contains the structural element of the formula II, or to mixtures of these salts,

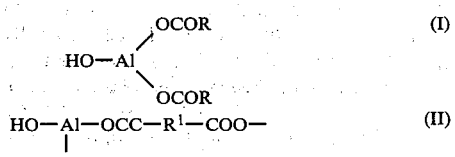

in which R is methyl, ethyl or phenyl or $R^1$ is the divalent group $-C_nH_{2n}-$, in which n is a number from 3 to 10.

The $-C_nH_{2n}-$ group is preferably a linear alkylene group. Preferred aluminium monohydroxide salts of a carboxylic acid which are free from water of crystallisation are aluminium monohydroxide dipropionate, aluminium monohydroxide dibenzoate, aluminium monohydroxide sebacate and especially aluminium monohydroxide diacetate and aluminium monohydroxide adipate.

The aluminium salts according to the invention surprisingly have an acicular to rod-shaped crystal form. They can have a length of 0.1 to 200 μm, a thickness of 0.01 to 10 μm and a length/thickness ratio of 5:1 to 50:1 and their density is about 1.3 to 1.7 g/cm³.

The present invention also relates to acicular to rod-shaped aluminium monohydroxide salts of a carboxylic acid, which are free from water of crystallisation and are obtained by reacting neutral or basic aluminium oxide or aluminium hydroxide with acetic acid, propionic acid, benzoic acid, a dicarboxylic acid of the formula $HO_2C-C_nH_{2n}-CO_2H$ or the anhydrides of these acids.

The salts of the formula I can be in the form of dimers. The salts containing the structural element of the formula II are in the main cyclic dimers. They can, however, also contain cyclic oligomers.

The aluminium salts according to the invention can be prepared in known industrial equipment, by reacting neutral or basic aluminium oxide or aluminium hydroxide with acetic acid, propionic acid, benzoic acid, a dicarboxylic acid of the formula $HO_2C-C_nH_{2n}-CO_2H$, in which n is a number from 3 to 10, or the acid anhydrides thereof, in the presence of an inert solvent or without a solvent, with the exclusion of water and at elevated temperatures, and continuously removing the water of reaction from the reaction mixture.

Suitable aluminium oxides and aluminium hydroxides are, for example, $Al_2O_3$, $Al(OH)_3$, $AlO(OH)$, $Al_2O_3 \cdot H_2O$ and $Al_2O_3 \cdot 3H_2O$. Freshly precipitated aluminium hydroxide is preferred. Suitable acids are, for example, acetic acid (glacial acetic acid), propionic acid, benzoic acid, glutaric acid, pimelic acid, suberic acid, azelaic acid, sebacic acid, adipic acid, trimethyladipic acid and decanedicarboxylic acid and also mixtures thereof.

The reaction temperatures are in general above 100° C.; preferably, the reaction is carried out at the boiling point of the solvent used. When monocarboxylic acids are employed, the solvent can be the acid itself, and this is then employed in a large excess. In this case, it is also possible simply to reflux the reaction mixture without removing the water of reaction. Drying is then effected in a conventional manner by, for example, washing with an alcohol and subsequently subjecting to a heat treatment in vacuo at temperatures above 100° C. in order to remove the residual water. In general, 2 to 3 mols of mono- or di-carboxylic acid or the anhydrides thereof are employed per gram atom of aluminium.

When acid anhydrides are used, the water of reaction is bonded as a result of the hydrolysis of the anhydrides.

The reaction mixtures are usually suspensions, so that it is advantageous to replenish the amounts of solvent distilled off. Examples of suitable solvents are benzene, xylene, chlorobenzene, dichlorobenzene, dimethylformamide, N-methylpyrrolidone and dimethylacetamide. When a solvent is used, the water formed can be distilled off as an azeotrope. The desired acicular to rod-shaped crystals are obtained in a purer form when a solvent is used than when the preparation is carried out by the melt process, and this is more advantageous inasmuch as expensive separation operations are avoided.

Moreover, the reaction times are generally shorter when solvents are used. The progess of the reaction can be followed microscopically on the basis of the formation of the acicular to rod-shaped crystalline product. In general, reaction times of at least 10 hours are required with this process to achieve complete conversion.

Aluminium acetates and aluminium propionates tend to undergo decomposition by hydrolysis in the presence of water, but the benzoates and dicarboxylic acid salts do not show this tendency, so that water can also be used as the solvent for the latter. In this case, it is even possible, in order to prepare salt mixtures, also to use mixtures of acetic acid or propionic acid with benzoic acid or the dicarboxylic acids. This reaction can also be carried out under pressure. With this process, the procedure employed can be to warm or reflux the reaction mixture for some time in an autoclave. The resulting acicular to rod-shaped crystalline product is then filtered off in the customary manner, dried by washing with alcohols and then subjected to a heat treatment in order to remove the residual water, this treatment advantageously being carried out in vacuo. Temperatures of above 100° C. are preferably used.

Furthermore, it is possible to prepare the aluminium monohydroxide salts, of dicarboxylic acids, according to the invention by reacting water-containing or anhydrous aluminium monohydroxide diacetate, or other corresponding salts of weak acids, with dicarboxylic acids $HO_2C—C_nH_{2n}—CO_2H$, the weaker acid being driven off. The reaction can be carried out in the melt or using solvents.

The present invention also relates to the crystalline products prepared by these processes.

Because of their relatively low specific weight and their acicular to rod-shaped crystal form, the aluminium monohydroxide salts, of carboxylic acids, according to the invention, which can also be in the form of dimers, are outstandingly suitable as fillers, especially reinforcing fillers in plastics.

In some cases, for example elastomers, pronounced reinforcing effects are already observed when relatively small amounts are added (for example about 5% by weight). In other cases, larger amounts must be incorporated. The plastics can contain 1 to 80% by weight and preferably 2 to 60% by weight, based on the plastic.

Plastics which can be used are both thermosetting plastics and thermoplastics. Examples are:

1. Polymers which are derived from mono- or di-unsaturated hydrocarbons, such as polyolefins, for example polyethylene, which can be crosslinked, polypropylene, polyisobutylene, polymethylbut-1-ene, polymethylpent-1-ene, polybut-1-ene, polyisoprene, polybutadiene, polystyrene and polyisobutylene, copolymers of the monomers on which the said homopolymers are based, such as ethylene/propylene copolymers, propylene/but-1-ene copolymers and propylene/isobutylene copolymers, and also terpolymers of ethylene and propylene with a diene, for example hexadiene, dicyclopentadiene or ethylidenenorbornene; and mixtures of the abovementioned homopolymers, for example mixtures of polypropylene and polyethylene, of polypropylene and polybut-1-ene and of polypropylene and polyisobutylene.

2. Halogen-containing vinyl polymers, such as polyvinyl chloride, polyvinylidene chloride and polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, and also their copolymers with other vinyl compounds, such as acrylonitrile/butadiene/styrene, acrylonitrile/styrene and acrylonitrile/styrene/acrylate copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate and polyallylmelamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers. In this group, elastomeric epoxide resins are particularly preferred.

6. Polyacetals, such as polyoxymethylene and polyoxyethylene, and also those polyoxymethylenes which contain ethylene oxide as the comonomer.

7. Polyphenylene oxides.

8. Polyurethanes and polyureas.

9. Polycarbonates.

10. Polysulfones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Crosslinked polymers which are derived from aldehydes on the one hand and from phenols, ureas and melamines on the other hand, such as phenol-formaldehyde resins, urea-formaldehyde resins and melamine-formaldehyde resins.

13. Alkyd resins, such as glycerol/phthalic acid resins and their mixtures with melamine-formaldehyde resins.

14. Unsaturated polyester resins which are derived from copolyesters of saturated and unsaturated dicarboxylic acids with polyhydric alcohols, and vinyl compounds as crosslinking agents.

15. Naturally occurring polymers, such as cellulose and rubber, and also their polymer-homologously chemically modified derivatives, such as cellulose acetates, cellulose propionates and cellulose butyrates and the cellulose ethers, such as methylcellulose.

16. Thermoplastic polyesters based on aliphatic, cycloaliphatic and/or aromatic dicarboxylic acids and diols, for example polyethylene terephthalate, polybutylene terephthalate or copolyesters thereof.

The incorporation of the filler according to the invention and, if desired, further additives can be effected, for example, by mixing in the individual additives, together or individually, and if desired further additives, by the methods customary in industry, before or during shaping, or by applying the dissolved or dispersed compounds to the polymer, with subsequent evaporation of the solvent if necessary. The additives, for example up to 10% by weight, can also be added before or during the polymerisation. Larger amounts are advantageously incorporated by regranulating in an extruder.

Examples of further additives and inert adjuncts, together with which the filler can be employed, are anti-oxidants, UV stabilisers or other light stabilisers, plasticisers, glidants, mould release assistants, crystal seed-forming agents, fluorescent brighteners, delustering agents, dyes and pigments, inert or reinforcing fillers, such as carbon black, talc, kaolin, metal powders, wollastonite, glass balls or glass powder, quartz powder, asbestos fibres and glass fibres, and dispersing assistants.

It has been found that, especially in the range of the thermosetting plastics, it is possible, by reason of the relatively low specific weight, to prepare suspensions which are stable on storage over a prolonged period from the filler according to the invention and a curable mixture, as a result of which a uniform distribution of the filler in the cured moulding is ensured.

The examples which follow illustrate the invention in more detail. Analytical results which deviate from the calculated value are due to incomplete reaction and are caused by a content of the aluminium compound used as the starting material. This has only a slight influence on the characteristics of the products as fillers. The percentages are by weight.

EXAMPLE 1

273 g (3.5 mols) of aluminium hydroxide, hydrargillite (Merck, finely powdered) are added, with stirring, to 2,100 g (35 mols) of acetic acid in a 4.5 liter sulfonation flask, provided with a stirrer, a thermometer and a distillation head with a descending condenser, and the mixture is heated, whereupon aqueous acetic acid starts to distil off slowly at an internal temperature of 114° C. (bath temperature of 130° C.). In order to ensure that the mixture remains stirrable and to replenish the acetic acid distilled off, a total further amount of 1,000 ml of fresh acetic acid is added, in portions of 100 ml, in the course of the entire reaction period of 72 hours. The progress of the reaction can be followed without difficulty under a microscope and the insoluble product is finally in the form of fine needles.

It is filtered off hot and is 4 times stirred with, in each case, 2,000 ml of isopropanol at 70° C. and filtered off and is then dried at 100° C./13.3 Pa. 553 g of a colourless, fine acicular product with a density of 1.64 g/cm$^3$ are obtained. The length of the needles is 0.3 μm–1.9 μm and the width 0.02 μm–0.5 μm.

Elementary analysis: Found: C, 29.10%; H, 4.20%; Al, 16.35%; Calculated: C, 29.63%; H, 4.36%; Al, 16.61%.

It can be concluded from the composition and from the IR spectra that the structure is that of AlOH(O$_2$CCH$_3$)$_2$.

This aluminium monohydroxide diacetate is broken down by boiling water, liberating acetic acid which, after the aluminium hydroxide precipitated has been filtered off, is determined quantitatively by titration with dilute sodium hydroxide solution. The result supports the indicated structure.

EXAMPLE 2

1,020 g (10 mols) of acetic anhydride are initially introduced into a 1.5 liter sulfonation flask, provided with a stirrer, a thermometer and a reflux condenser, and 39 g (0.5 mol) of aluminium hydroxide, hydrargillite (Merck, finely powdered) are added, with stirring. The reaction mixture is brought to the reflux temperature in the course of 2 hours. After a reaction time of 72 hours under the indicated conditions, all of the product is in the form of microscopically fine needles. After cooling, the reaction mixture is filtered. The filter residue is 4 times washed with, in each case, 100 ml of isopropanol at 70° C. and filtered off and is then dried at 100° C. under 13.3 Pa. 70 g of a colourless, finely acicular product are obtained.

Elementary analysis: Found: C, 29.11%; H, 4.42%; Al, 17.0%; Calculated: C, 29.63%; H, 4.36%; Al, 16.61%.

EXAMPLE 3

39 g (=0.5 mol) of aluminium hydroxide, hydrargillite (Merck, finely powdered) are added, with stirring, to 445 g (=6.0 mols) of pure propionic acid (Fluka) in a 1.5 liter sulfonation flask, provided with a stirrer, a thermometer and a distillation head with a descending condenser, and the mixture is heated. The propionic acid starts to distil off slowly at a bath temperature of 160° C. and an internal temperature of about 136° C. In order to ensure that the mixture remains stirrable, the propionic acid distilled off (900 ml) is continuously replenished with a total of 1,500 ml of fresh propionic acid in the course of the entire reaction period of 96 hours. The increasing occurrence of the rod-shaped product as the reaction time proceeds can be followed under a microscope. For working up, the hot reaction mixture is filtered with suction and the filter residue is 4 times stirred with, in each case, 1,000 ml of isopropanol at about 70° C. and filtered off. The product is then dried in a vacuum drying cabinet at 100° C./13.3 Pa. 78 g of a colourless, rod-shaped product result. Density: 1.40 g/cm$^3$. Specific surface area: 9 m$^2$/g. Length of the rods: 0.5–3.5 μm. Width: 0.2–1 μm.

Elementary analysis: Found: C, 37.53%; H, 5.97%; Al, 14.30%; Calculated: C, 37.93%; H, 5.84%; Al, 14.20%.

The analysis and the IR spectrum characterise the product as aluminium monohydroxide dipropionate.

EXAMPLE 4

Analogously to Example 1, 976 g (8 mols) of benzoic acid, dissolved in 3,500 ml of o-dichlorobenzene, are initially introduced into a 6 liter sulfonation flask and 156 g (2 mols) of aluminium hydroxide, hydrargillite (Merck, finely powdered) are suspended in this solution. The mixture is now heated until the distillation of water-containing dichlorobenzene starts at an internal temperature of 175° C. (Distillation temperature 160° C.). The dispersion, which initially is of low viscosity, becomes ever more viscous and in the course of the total reaction time of 96 hours has twice to be diluted with 500 ml of fresh o-dichlorobenzene. In total, 800 ml of a two-phase, water-containing distillate are obtained. The reaction mixture is now filtered whilst it is still hot and the residue is 4 times stirred with 6 liters of isopropanol and filtered off. The product purified in this way is dried at 100°/2 kPa. 497 g of a colourless, fine, acicular product are obtained.

Elementary analysis: Found: C, 55.06%; H, 3.90%; Al, 10.85%; Calculated: C, 58.74%; H, 3.87%; Al, 9.43%.

EXAMPLE 5

224 g (=2.0 mols) of benzoic acid, 25.5 g (=0.25 mol) of aluminium oxide and 500 ml of o-dichlorobenzene are heated, with stirring, in a 1.5 liter sulfonation flask provided with a stirrer, a thermometer and a distillation head with a descending condenser. At a bath temperature of 190° C. and an internal temperature of about 178° C., the whole can be reacted in the course of 94 hours, a distillate with a total volume of about 100 ml being obtained in the course of the reaction. The hot suspension is then filtered and the filter residue is 4 times warmed with, in each case, 500 ml of isopropanol at 70° C. and filtered off. The product purified in this way is dried at 100° C./2 kPa. 35 g of a product which contains acicular crystals are obtained. The result of the analysis indicates that, compared with Example 4, there is still a high proportion of unconverted Al$_2$O$_3$.

Elementary analysis: C, 20.65%; H, 1.50%; Al, 39.85%.

EXAMPLE 6

273 g (3.5 mols) of aluminium hydroxide (hydrargillite) and 2,120 g (35 mols) of acetic acid are initially introduced into a 3 l sulfonation flask with a distillation head and a descending condenser. The reaction mixture is warmed to 115° C., the water formed being distilled off and the acetic acid distilled off being replenished (total 750 ml).

After 45 hours, the reaction mixture is cooled to room temperature and filtered through a suction filter and the filter residue is suspended several times with a total of 3.5 l of isopropanol and filtered off. The resulting product is dried for 12 hours in a vacuum cabinet at 130° C. 552 g (98%) of acicular aluminium monohydroxide diacetate result.

EXAMPLE 7

31.2 g (0.4 mol) of Al(OH)$_3$ hydrargillite and 378 g of glacial acetic acid are initially introduced into a 750 ml sulfonation flask provided with a stirrer, a thermometer and a reflux condenser. The mixture is refluxed for 24 hours. After this time, the reaction product is cooled and filtered off and is 4 times suspended with, in each case, 50 ml of isopropanol and filtered off. The product is then dried in a vacuum cabinet at 130° C. 61.2 g (94.5% of theory) of acicular aluminium monohydroxide diacetate result.

EXAMPLE 8

245.0 g of acetic anhydride and 48.0 g of acetic acid (100%) are added to 62.4 g (0.8 mol) of aluminium hydroxide, hydrargillite, Merck, in a 750 ml sulfonation flask, provided with a thermometer, a reflux condenser and a stirrer, and the mixture is heated to 125° C., with stirring. After a reaction time of 12 hours, the reaction product is cooled, filtered off, washed with 4 times 250 ml of water and dried for 12 hours at 130° C./15 mm Hg; 124 g (95.6%) of acicular aluminium monohydroxide diacetate are obtained.

EXAMPLE 9

39.0 g (0.5 mol) of aluminium hydroxide (hydrargillite), 244 g (2.0 mols) of benzoic acid and 500 ml of water are introduced into a 1 l steel autoclave provided with a stirrer. The mixture is heated at 170° C./15 bars for 12 hours. After cooling, the reaction product is filtered off and the filter residue is 4 times warmed with, in each case, 1.5 l of isopropanol to 70° C. and filtered off. After drying in a vacuum cabinet at 100° C. under 80 mm Hg, 134.1 g (93.7%) of crystalline aluminium monohydroxide dibenzoate are obtained (needles, length 0.15–2μ, width 0.05–0.25μ). Density: 1.41±0.03 g/cm$^3$. Specific surface area 60.4±1.2 m$^2$/g Elementary analysis: found: C, 57.84; H, 3.915; Al, 9.47%; calculated: C, 58.74; H, 3.87; Al, 9.43%.

IR spectrum (KBr): 3,700 (OH), 3,060, 3,020 (CH=CH), 1,610, 1,570, 1,500, 1,430 (aryl) cm$^{-1}$.

EXAMPLE 10

2 liters of o-dichlorobenzene are initially introduced into a 6 liter sulfonation flask, provided with a stirrer, a thermometer and a distillation head with a descending condenser, and 1,168 g (8 mols) of adipic acid are suspended therein. The mixture is then heated, with stirring, until, at an internal temperature of 150°–155° C., a homogeneous solution has formed, and 312 g (4 mols) of aluminium hydroxide, Al(OH)$_3$, are then added. The temperature of the reaction mixture is now further raised until aqueous o-dichlorobenzene starts to distil off at 170° C. The progress of the reaction is indicated by a continuous increase in the amount of suspended substance and by the fact that the mixture becomes more difficult to stir. During the total reaction period of 96 hours, 2,100 ml of water-containing o-dichlorobenzene are distilled off. This amount is replenished by the continuous addition of 4,200 ml of o-dichlorobenzene. The increasing occurrence of the acicular product as the reaction time proceeds can be followed under a microscope. The working up, the hot reaction mixture is filtered with suction and the filter residue is 4 times stirred with 6 liters of isopropanol at 75° C. and filtered off. The product purified in this way is dried for 48 hours at 100° C./2 kPa. 723 g of a colourless, acicular product result. Elementary analysis: C, 37.46%, H, 5.11%, Al, 14.10%. The length of the needles varies between 0.1 and 4.0 μm and their width varies between 0.05 and 0.15 μm. The density determined was 1.40 g/cm$^3$ and the specific surface area determined (by the Brunauer, Emmett and Teller method of nitrogen adsorption) was 2.81 m$^2$/g. The product starts to decompose at 410° C. (thermogravimetric analysis TGA, under air).

EXAMPLE 11

438 g (3 mols) of adipic acid are added to 100 ml of dimethylformamide. The slurry-like mixture is warmed to 130° C., whereupon a homogeneous solution forms. 51 g (0.5 mol) of aluminium oxide (activity level I, basic, from JCN Pharmaceuticals GmbH, Eschwege, Germany) are added to the solution. Warming of the mixture is continued until it starts to reflux gently. The reaction mixture rapidly becomes viscous, so that after a reaction time of 4 hours a further 550 ml of dimethylformamide have to be added so that the mixture remains readily stirrable. The reaction is then continued under gentle reflux for a further 43 hours. The mixture is then filtered hot and the filter residue is 4 times stirred with, in each case, 1.5 liters of isopropanol and filtered off and finally is dried to constant weight at 100° C./13.3 Pa. 168.6 g of a colourless, acicular product result.

Elementary analysis: C, 35.70%; H, 4.68%; Al, 15.90%.

EXAMPLE 12

264 g (=2.0 mols) of glutaric acid are added, with stirring, to 300 ml of o-dichlorobenzene in a 1.5 liter sulfonation flask, provided with a stirrer, a thermometer and a distillation head with a descending condenser, and the mixture is heated. At 153° C., the glutaric acid has melted but has not dissolved in the solvent. 78 g (=1.0 mol) of aluminium hydroxide are now stirred into the mixture and the latter is further heated up to a bath temperature of 200° C. and an internal temperature of about 177° C. During this heating period, at about 168° C., o-dichlorobenzene starts to distil off as an azeotrope with water which is eliminated. The reaction proceeds over 7 days and in total 2,200 ml of distillate are obtained. A total of 3,800 ml of fresh o-dichlorobenzene are added continuously, so that the reaction mixture always remains readily stirrable. After 4 days, the first acicular crystals are detected in the reaction mixture when this is checked under a microscope. After the reaction time has ended, the hot suspension is filtered. The filter residue is 4 times warmed with, in each case, 1.5 liters of isopropanol to 70° C., with stirring, and filtered off. The product is then dried in a vacuum drying cabinet at 100° C./2 kPa. The yield is 165 g of an acicular product.

Elementary analysis: C, 34.29%; H, 4.10%; Al, 16.40%.

EXAMPLE 13

160 g (=1.0 mol) of pimelic acid and 39 g (=0.5 mol) of aluminium hydroxide hydrargillite (from Merck, finely powdered) are suspended in 400 ml of o-dichlorobenzene in a 1.5 liter sulfonation flask. The mixture is heated until, at an internal temperature of about 177° C., the distillation of water-containing o-dichlorobenzene starts. The suspension, which initially is of low viscosity, becomes ever more viscous and in the course of the total reaction period of 30 hours it is necessary to replenish the total 870 ml of water-containing o-dichlorobenzene, which is distilled off, by fresh o-dichlorobenzene. The hot suspension is now filtered and the filter residue is 4 times heated with 2 liters of isopropanol to 70° C., with stirring, and filtered off. The product is then dried in a vacuum drying cabinet at 100° C./2 kPa. 100 g of a colourless, fine, acicular product are obtained.

Elementary analysis: C, 39.98%; H, 5.51%; Al, 12.90%.

EXAMPLE 14

174 g (=1.0 mol) of suberic acid are suspended in 400 ml of o-dichlorobenzene in a 1.5 liter sulfonation flask, provided with a stirrer, a thermometer and a distillation head with a descending condenser, and the suspension is heated. After all of the suberic acid has dissolved, at an internal temperature of about 122° C., 39 g (=0.5 mol) of aluminium hydroxide are added, with stirring, and the mixture is further heated up to an internal temperature of 177° C. The water-containing o-dichlorobenzene then starts to distil off slowly. After a reaction period of 20 hours, the reaction mixture is a viscous suspension and this is rendered readily stirrable again with 400 ml of fresh o-dichlorobenzene. In order to keep the reaction mixture readily stirrable, fresh o-dichlorobenzene (total 1,200 ml) is added continuously to replenish the distillate (total 550 ml). After a total reaction time of 48 hours, the hot suspension is filtered and the filter residue is 4 times warmed with 1.5 liters of isopropanol to 70° C., with stirring, and then filtered off and dried in a vacuum drying cabinet at 100° C./13.3 Pa. 88 g of a colourless, fine, acicular product are obtained.

Elementary analysis: C, 39.49%; H, 5.63%; Al, 14.85%.

Density: 1.39 g/cm$^3$. Specific surface area (BET): 38.2 m$^2$/g.

EXAMPLE 15

188 g (=1.0 mol) of azelaic acid (Merck-Schuchardt) are suspended in 400 ml of o-dichlorobenzene in a 1.5 liter sulfonation flask and the suspension is heated until, at an internal temperature of 108° C., everything has dissolved to give a clear solution. 39 g (=0.5 mol) of aluminium hydroxide, hydrargillite, are suspended in this solution and the suspension is further heated up to a bath temperature of about 200° C. and an internal temperature of about 177° C., whereupon the water-containing o-dichlorobenzene starts to distil off. The reaction mixture becomes increasingly more viscous in the course of the reaction period (total 96 hours). In order to maintain good stirrability, the moist distillate (total 610 ml) is replenished and additional o-dichlorobenzene (total 1,150 ml) is added to the mixture. The mixture is now filtered whilst it is still hot and the residue is 4 times warmed with, in each case, 1 liter of isopropanol to 75° C. and filtered off and dried in a vacuum cabinet at 100° C./2 kPa. The yield is 101 g of a fine, acicular product.

Elementary analysis: C, 44.10%; H, 6.48%; Al, 13.05%.

EXAMPLE 16

720 ml of dimethylformamide and 1,454.4 g of sebacic acid are heated, with stirring, in a 4.5 liter sulfonation flask, provided with a stirrer, a thermometer and a distillation head with a descending condenser, until, at about 135°–140° C., everything has dissolved. 122.5 g of aluminium oxide ("WOELM", basic, from ICN Pharmaceuticals GmbH+Co., Eschwege) are then stirred in. The bath temperature is then raised and the distillation of water-containing dimethylformamide starts at an external temperature of 200° C. and an internal temperature of 177° C. (temperature of the distillate 130° C.). After 5 hours, 90 cm$^3$ of water-containing dimethylformamide have distilled over. When the reaction is continued, the reaction mixture increasingly changes to a thick paste and after a further 12 minutes this is reconverted to a readily stirrable form by the addition of 800 ml of dimethylformamide, whereupon distillation again takes place at an increased rate. After a total reaction period of 48 hours, 470 ml of water-containing dimethylformamide have distilled off. The reaction mixture then consists virtually only of an acicular product; all of the aluminium oxide has been consumed. In order to improve suspension and filtration, a further 1,500 ml of fresh dimethylformamide are added and the suspension is filtered whilst it is still hot. The residue is 4 times stirred with, in each case, about 2 liters of isopropanol at 70° C. and filtered off and is then dried in a vacuum drying cabinet at 100° C./13.3 Pa. 418.5 g of a colourless, acicular product result.

Elementary analysis: C, 43.51%; H, 6.30%; Al, 13.9%.

EXAMPLE 17

400 ml of o-dichlorobenzene and 403.6 g (=2.0 mols) of sebacic acid are heated, with stirring, in a 1.5 liter sulfonation flask, provided with a stirrer, a thermometer and a distillation head with a descending condenser, until, at about 126° C., everything has dissolved to give a clear solution. 78 g (=1.0 mol) of aluminium hydroxide, hydrargillite, are then stirred in and the mixture is further heated. At a bath temperature of 200° C. and an internal temperature of about 183° C., the water-containing o-dichlorobenzene starts to distil off (distillation temperature about 130°–140° C.). The suspension becomes ever more viscous in the course of the reaction period and good stirrability is maintained by replenishing the distillate (2,750 ml) and adding fresh o-dichlorobenzene (total 3,050 ml). The course of the reaction is monitored by observing the crystal form under a microscope and after a reaction period of 27 hours the majority of the crystals are already beautiful, fine, acicular crystals. After 96 hours, the reaction mixture consists virtually only of the acicular product. The hot suspension is now filtered and the residue is 4 times warmed with, in each case, 200 ml of isopropanol to 70° C., stirred well and filtered off. After drying the substance in a vacuum drying cabinet at 100° C./2 kPa, 128 g of an acicular product are obtained.

Elementary analysis: C, 42.72%; H, 6.51%; Al, 13.30%.

Density: 1.34 g/cm$^3$; specific surface area: 26.7 m$^2$/g.

EXAMPLE 18

39 g (=0.5 mol) of aluminium hydroxide, hydrargillite, and 230 g (=1.0 mol) of decanedicarboxylic acid, purum (Fluka), are suspended in 400 ml of o-dichlorobenzene by heating to 177° C. in a 1.5 liter sulfonation flask, provided with a stirrer, a thermometer and a distillation head with a descending condenser. At this internal temperature, the water-containing o-dichlorobenzene slowly starts to distil off azeotropically. The suspension becomes viscous after a reaction time of 20 hours. The good stirrability of the mixture is maintained by continuously replenishing the distillate (600 ml) and adding fresh o-dichlorobenzene (total 850 ml). After a reaction time of 80 hours, the hot suspension is filtered and the filter residue is 4 times washed with, in each case, 1 liter of isopropanol at 70° C. and filtered off and is then dried at 110° C./13.3 Pa. 73.4 g of a fine, acicular product result.

Elementary analysis: C, 35.50%; H, 6.50%; Al, 16.70%.

Density: 1.42 g/cm$^3$; Specific surface area: 22.5 m$^2$/g.

EXAMPLE 19

500 g (0.5 mol) of a freshly prepared suspension of Al(OH)$_3$ in water are heated with 146 g (1.0 mol) of adipic acid and 500 ml of water to 180° C. in a 2.5 l steel autoclave, provided with a stirrer and a thermometer, and the mixture is stirred for 12 hours under a pressure of 15 bars. After the reaction has ended, the mixture is cooled to room temperature and filtered. The residue is 4 times warmed with, in each case, 1.5 l of isopropanol to 70° C., suspended and filtered off and is dried for 12 hours at 100° C./0.05 mm Hg. 85 g (90.38%) of colourless needles are obtained.

Density: 1.48±0.04 g/cm$^3$; specific surface area: 13.3±0.3 m$^2$/g

Found: C, 37.32; H, 4.70; Al, 14.00; Calculated: C, 38.31; H, 4.82; Al, 14.34.

IR spectrum (KBr): 3,700 (—OH), 2,960 (-CH$_2$—), 1,600 (CO) cm$^{-1}$.

On the basis of the elementary analysis and the IR spectrum, the product is to be designated aluminium monohydroxide adipate.

EXAMPLE 20

500 g (0.05 mol) of a freshly prepared suspension of Al(OH)$_3$ in water, 202 g (1.0 mol) of sebacic acid and 500 ml of water are introduced into a 2.5 l steel autoclave provided with a stirrer and a thermometer. The mixture is heated to 180° C. under a pressure of 14 bars and is stirred at this temperature for 12 hours. After cooling, the reaction mixture is filtered and the residue is 4 times warmed with, in each case, 1.5 l isopropanol to 70° C. and filtered off and is dried at 100° C./0.05 mm Hg for 12 hours. 100.6 g (82.39%) of colourless needles are obtained.

Density: 1.31±0.02 g/cm$^3$ Specific surface area: 50.4±1.0 m$^2$/g

Found: C, 48.05; H, 6.79; Al, 11.70; Calculated: C, 49.18; H, 7.02; Al, 11.05.

IR spectrum (KBr): 3,700 (—OH), 2,960 (—CH$_2$—), 1,600 (CO), 1,520 cm$^{-1}$.

On the basis of the elementary analysis and the IR spectrum, the product is to be designated aluminium monohydroxide sebacate.

EXAMPLE 21

31.2 g of Al(OH)$_3$ (hydrargillite, 0.4 mol), 116.9 g (0.8 mol) of adipic acid and 300 g of water are initially introduced into a 750 ml sulfonation flask, provided with a reflux condenser, a thermometer and a stirrer, and the mixture is refluxed for 24 hours. After the reaction has ended, the reaction mixture is filtered and the product is washed several times with isopropanol. The product is then dried for 12 hours at 130° C. in a vacuum cabinet. 39.3 g of acicular, crystalline, colourless aluminium monohydroxide adipate result.

EXAMPLE 22

31.2 g (0.4 mol) of Al(OH)$_3$, hydrargillite, 116.9 g (0.8 mol) of adipic acid, 30.0 g of water and 270 g (4 5 mols) of glacial acetic acid are initially introduced into a 750 ml sulfonation flask, provided with a stirrer, a reflux condenser and a thermometer, and the mixture is refluxed for 24 hours. After the reaction has ended, the product is filtered off, several times suspended with hot isopropanol and filtered off and dried for 12 hours in a vacuum cabinet at 130° C. 57.5 g of colourless, crystalline needles result.

The acetic acid derivative is decomposed in water (the adipic acid derivative is stable in water) and the content of acetic acid derivative is determined as follows:

An accurately weighed amount of the product mixture is heated in distilled water at 90° C. for 15 hours, with stirring, during which time complete hydrolysis of the acetic acid derivative takes place. The adipic acid salt, which has not dissolved, and the aluminium hydroxide formed are then filtered off and the acetic acid formed is titrated against 0.1 N sodium hydroxide solution. The adipic acid derivative is then saponified by vigorous hydrolysis with 1 N NaOH for 1 hour at 70° C. and the adipic acid formed is determined using 1 N hydrochloric acid.

According to this analytical method of determination, the product prepared by the above method contains 40% by weight of the adipic acid derivative and 46.5% by weight of the acetic acid derivative, as well as 8% by weight of unconverted aluminium hydroxide.

EXAMPLE 23

124.8 g (1.6 mols) of Al(OH)$_3$, hydrargillite, 467.5 g (3.2 mols) of adipic acid, 120 g of water and 1,080 g of acetic acid are initially introduced into a 2.5 l sulfonation flask provided with a porcelain stirrer, a reflux condenser and a thermometer. The mixture is refluxed for 64 hours, then allowed to cool and filtered and the product is washed 4 times with isopropanol. zhe product is then dried for 12 hours in a vacuum cabinet at 130° C. 260 g of colourless, fine crystalline needles result.

According to the analytical method indicated in Example 22, the product described above consists of 36% by weight of the adipic acid derivative and 58% by weight of the acetic acid derivative.

USE EXAMPLES

Example I 68.7 g (=0.1 equivalent) of an acid adipic acid/-neopentylglycol polyester are warmed to 110° C. and mixed well with 16.7 g (=0.1 equivalent) of a triepoxide of the following formula III

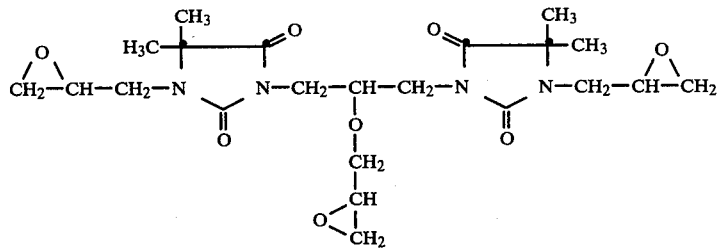
(III)

and 0.18 g of 1-methylimidazole: Mixture A. Glass fibres (to give mixture B) or diverse amounts of an acicular additive (to give mixtures C, D and E) are mixed into portions of this mixture. After removing the air in vacuo, the mixtures are poured into the 1 mm thick Al moulds. After curing for 16 hours at 140° C., mouldings with the following properties are obtained:

|  | A | B | C | D | E |
|---|---|---|---|---|---|
| Tensile strength: | 1.45 | 2.3 | 2.8 | 4.7 | 6.8 N/mm² |
| Elongation at break: | 119 | 111 | 158 | 83 | 182 % |
| Toughness: | 0.96 | 1.3 | 2.2 | 1.9 | 6.2 N/mm² |
| Tear propagation resistance: | 3.1 | 5.5 | 4.5 | 10.3 | 14.1 N/mm |
| Modulus of elasticity: | 1.3 | 3.8 | 2.8 | 7.1 | — |

A = without additive (comparison)
B = with the addition of 7% of glass fibres + 2% of "Aerosil"* (comparison)
C = with the addition of 2% of the reaction product of aluminium oxide and adipic acid according to Example 11
D = with the addition of 7% of the reaction product of aluminium oxide and adipic acid according to Example 11
E = with the addition of 10% of the reaction product of aluminium oxide and adipic acid according to Example 11

Toughness = $\frac{\text{tensile strength} \times \text{elongation at break}}{2}$

*When glass fibres are added, a small amount of an agent imparting thixotropic properties must be added since otherwise extensive sedimentation takes place during processing.

Example II

An acid polyester is prepared from 23 mols of adipic acid and 22 mols of neopentylglycol by the melt process. The polyester has an acid equivalent weight of 1,532.

9 g (=about 6% by weight) of aluminium adipate needles according to Example 11 are incorporated into 153 g (=0.1 equivalent) of the polyester on a three-roll mill and the polyester is warmed to 130° C. and mixed well with 11.0 g (=0.1 equivalent) of triglycidyl isocyanurate. After cooling to about 100° C., 0.3 g of an accelerator having the following structure

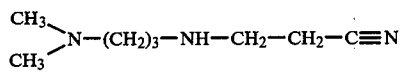

is added and the whole is mixed well. The mixture is processed as in Example I. The following values were measured:

tensile strength=10.0 N/mm² (2.4); elongation at break=760% (368).

The values for the epoxide resin which has not been reinforced are given in brackets. The resulting elastomer displays pronounced rubbery and elastic characteristics. The high elasticity of the elastomeric epoxide resin is further improved by the addition of the needles, whilst the tensile strength is even increased by a factor of 4.

What is claimed is:

1. An acicular to rod-shaped aluminium monohydroxide salt of a carboxylic acid, which salt is free from water of crystallisation and has the formula I or contains the structural element of the formula II, or mixtures of these salts,

(I)

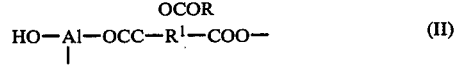
(II)

in which R is methyl, or ethyl or R¹ is the divalent group —$C_nH_{2n}$—, in which n is a number from 3 to 10.

2. An aluminium salt according to claim 1, wherein the divalent —$C_nH_{2n}$— group is a linear alkylene radical.

3. Aluminium monohydroxide diacetate according to claim 1.

4. Aluminium monohydroxide dipropionate according to claim 1.

5. Aluminium monohydroxide sebacate according to claim 1.

6. Aluminium monohydroxide adipate according to claim 1.

7. A process for the preparation of an aluminium salt according to claim 1, by reacting neutral or basic aluminium oxide or aluminium hydroxide with acetic acid, propionic acid or HO₂C—$C_nH_{2n}$—CO₂H, in which n is a number from 3 to 10, or the acid anhydrides thereof, in the presence of an inert solvent or without a solvent, with the exclusion of water and at elevated temperatures, wherein the water of reaction is removed continuously from the reaction mixture.

8. A process according to claim 7, wherein the water of reaction is removed by distillation.

* * * * *